United States Patent [19]

Jensen

[11] Patent Number: 5,065,754
[45] Date of Patent: Nov. 19, 1991

[54] ASPIRATING CATHETER TUBE INSERTER

[75] Inventor: Billy M. Jensen, Sandy, Utah

[73] Assignee: Ballard Medical Products, Draper, Utah

[21] Appl. No.: 534,079

[22] Filed: Jun. 6, 1990

[51] Int. Cl.⁵ ............................................. A61M 16/00
[52] U.S. Cl. ............................ 128/200.26; 128/207.14; 128/912; 128/DIG. 26
[58] Field of Search ................... 128/207.14, 207.15, 128/207.16, 200.26, 912, DIG. 26; 604/171, 249

[56] References Cited

U.S. PATENT DOCUMENTS

| | | | |
|---|---|---|---|
| 113,503 | 4/1871 | Dinnen | 251/335.2 |
| 274,447 | 3/1883 | Kennish | 251/143 |
| 580,574 | 4/1897 | Fowler | 251/100 |
| 1,120,549 | 12/1914 | Schellberg | 604/171 |
| 1,463,735 | 7/1923 | Varrieur | 251/100 |
| 1,672,114 | 6/1928 | Crow | 604/249 |
| 1,917,981 | 7/1933 | Kindl | 251/95 |
| 1,944,553 | 1/1934 | Freund | 128/229 |
| 2,187,586 | 1/1940 | Hooper | 128/224 |
| 2,212,334 | 8/1940 | Wallerich | 604/780 |
| 2,584,450 | 2/1952 | Holt et al. | 128/203 |
| 2,705,959 | 4/1955 | Elmore | 128/351 |
| 2,755,060 | 7/1956 | Twyman | 251/342 |
| 2,893,395 | 7/1959 | Buck | 128/349 |
| 2,895,708 | 7/1959 | Palumbo | 251/77 |
| 2,912,982 | 11/1959 | Barsky | 128/912 |
| 2,924,232 | 2/1960 | Michaels | 137/315 |
| 2,937,643 | 5/1960 | Elliot | 128/214 |
| 3,017,880 | 1/1962 | Brook | 128/29 |
| 3,039,463 | 6/1962 | Dickey, Jr. et al. | 128/207 |
| 3,070,132 | 12/1962 | Sheridan | 604/280 |
| 3,104,090 | 9/1963 | Callahan, Jr. | 251/278 |
| 3,175,557 | 3/1965 | Hammond | 128/207.14 |
| 3,207,472 | 9/1965 | Seltsam | 251/331 |
| 3,322,126 | 5/1967 | Rüsch et al. | 128/351 |
| 3,335,723 | 8/1967 | Waldman, Jr. | 128/214.4 |
| 3,363,629 | 1/1968 | Kuhn | 604/281 |
| 3,444,860 | 5/1968 | Harrell | 128/349 |
| 3,461,877 | 8/1969 | Morch | 128/351 |
| 3,485,234 | 12/1969 | Stevens | 604/281 |
| 3,508,554 | 4/1970 | Sheridan | 604/280 |
| 3,517,669 | 6/1970 | Buono et al. | 128/276 |
| 3,595,445 | 7/1971 | Burford et al. | 222/213 |
| 3,605,750 | 9/1971 | Sheridan et al. | 604/280 |
| 3,612,038 | 10/1971 | Halligan | 604/281 |
| 3,614,057 | 10/1971 | Hospe | 251/251 |
| 3,628,532 | 12/1971 | Magrath | 128/145.8 |
| 3,633,758 | 1/1972 | Moise | 604/281 |

(List continued on next page.)

FOREIGN PATENT DOCUMENTS 3307517 9/1984 Fed. Rep. of Germany.
560910 7/1924 France.

OTHER PUBLICATIONS

"Side Eye Position", a report concerning Suction Kits and Catheters; Davol Products, (undated).
Cathmark, item of literature, (date unknown).

(List continued on next page.)

Primary Examiner—Edgar S. Burr
Assistant Examiner—Aaron J. Lewis
Attorney, Agent, or Firm—Lynn G. Foster

[57] ABSTRACT

A novel aspirating catheter tube inserter, and related methods, which provides for incremental, facile, safe, and efficient unidirectional delivery of an aspirating catheter to the lung of a patient. The disclosed inserter comprises a movable housing which is non-compressibly reciprocally moved relative to a stationary housing to urge the catheter tube to move incrementally into the patient. The inserter comprises resiliently compressible, seizing and releasing washers which accommodate distal displacement of the catheter tube into the patient when the movable housing is linearly moved toward the patient, but seizes and holds the catheter tube from movement when the movable housing is retracted. The catheter seizing and releasing washers also release the catheter from further progress into the lung, when there is an impeding force of a predetermined magnitude which is caused by tissue engagement, to prevent injury. The seizing and releasing washers allow the catheter tube to be physically grasped and pulled proximally from the lungs of the patient.

13 Claims, 4 Drawing Sheets

U.S. PATENT DOCUMENTS

| | | | |
|---|---|---|---|
| 3,719,737 | 3/1973 | Vaillancourt | 604/281 |
| 3,730,179 | 5/1973 | Williams | 128/145.5 |
| 3,734,094 | 5/1973 | Calinog | 128/2.06 |
| 3,757,771 | 9/1973 | Ruegg et al. | 128/2.1 E |
| 3,774,604 | 11/1973 | Danielsson | 128/214.4 |
| 3,825,001 | 7/1974 | Bennet et al. | 128/214.4 |
| 3,885,561 | 5/1975 | Cami | 604/280 |
| 3,894,540 | 7/1975 | Bonner, Jr. | 128/349 R |
| 3,911,919 | 10/1975 | Raitte | 128/276 |
| 3,935,857 | 2/1976 | Co | 604/281 |
| 3,937,220 | 2/1976 | Coyne | 604/119 |
| 3,991,762 | 11/1976 | Radford | 128/207.16 |
| 4,015,336 | 4/1977 | Johnson | 32/33 |
| 4,022,219 | 5/1977 | Basta | 128/351 |
| 4,027,659 | 6/1977 | Slingluff | 604/280 |
| 4,036,210 | 7/1977 | Campbell et al. | 128/2 F |
| 4,047,527 | 9/1977 | Kelsen | 128/229 |
| 4,050,667 | 9/1977 | Kossett | 604/281 |
| 4,052,990 | 10/1977 | Dodgson | 128/207.14 |
| 4,062,363 | 12/1977 | Bonner, Jr. | 128/349 |
| 4,081,176 | 3/1978 | Johnson | 251/342 |
| 4,119,101 | 10/1978 | Igich | 128/351 |
| 4,122,591 | 10/1978 | Kramann et al. | 29/157 R |
| 4,152,017 | 5/1979 | Abramson | 128/207.14 |
| 4,170,996 | 10/1979 | Wu | 128/349 R |
| 4,193,406 | 3/1980 | Jinotti | 128/204.18 |
| 4,212,300 | 7/1980 | Meals | 128/276 |
| 4,225,371 | 9/1980 | Taylor et al. | 156/652 |
| 4,235,232 | 11/1980 | Spaven et al. | 128/214.4 |
| 4,240,417 | 12/1980 | Holever | 128/912 |
| 4,245,636 | 1/1981 | Sparks et al. | 128/214 R |
| 4,256,099 | 3/1981 | Dryden | 128/200.26 |
| 4,275,724 | 6/1981 | Behrstock | 604/281 |
| 4,300,550 | 11/1981 | Gandi et al. | 128/207.18 |
| 4,324,239 | 4/1982 | Gordon et al. | 128/274 |
| 4,326,520 | 4/1982 | Alley | 128/214.4 |
| 4,327,723 | 5/1982 | Frankhouser | 128/214.4 |
| 4,327,735 | 5/1982 | Hampson | 128/348 |
| 4,356,610 | 11/1982 | Hon et al. | 29/157 |
| 4,387,879 | 6/1983 | Tauschinski | 251/149.1 |
| 4,397,442 | 8/1983 | Larkin | 251/342 |
| 4,414,999 | 11/1983 | Basta | 137/240 |
| 4,426,062 | 1/1984 | Bowrom | 251/7 |
| 4,440,378 | 4/1984 | Sullivan | 251/117 |
| 4,451,257 | 5/1984 | Atchley | 604/119 |
| 4,456,223 | 6/1984 | Ebling | 251/342 |
| 4,457,487 | 7/1984 | Steigerwald | 251/117 |
| 4,459,982 | 7/1984 | Fry | 128/204.23 |
| 4,469,483 | 9/1984 | Becker et al. | 128/DIG. 21 |
| 4,497,468 | 2/1985 | Hubbard et al. | 251/117 |
| 4,534,542 | 8/1985 | Russo | 251/342 |
| 4,537,387 | 8/1985 | Danby et al. | 251/331 |
| 4,595,005 | 6/1986 | Jinotti | 128/205.24 |
| 4,632,112 | 12/1986 | Matthews | 128/305.3 |
| 4,638,539 | 1/1987 | Palmer | 128/207.16 |
| 4,655,752 | 4/1987 | Honkanen et al. | 604/256 |
| 4,671,291 | 6/1987 | Wilson | 604/280 |
| 4,673,393 | 6/1987 | Suzuki et al. | 604/167 |
| 4,696,305 | 9/1987 | von Berg | 128/673 |
| 4,703,775 | 11/1987 | Pastrone | 137/625.3 |
| 4,704,111 | 11/1987 | Moss | 604/280 |
| 4,838,255 | 6/1989 | Lambert | 128/202.16 |

OTHER PUBLICATIONS

Superior Brochure, "Continuous Ventilating Suction System", (undated).

Superior Advertisement, "Infection Control Valve Suction Catheter", (undated).

Suctioning of Left Bronchial Tree in the Intubated Adult, *Care Medicine*, Kamiaru; 092, (date unknown).

Evaluation of Selective Bronchial Suctioning Techniques Used for Infants and Children, Anesthesiology, 48:379-380, (date unknown).

ACMI Catalog, pp. 31-35, Copyright 1960.

Prevention of Hypoxic Complication, 1968.

"Sterile Suctioning with Bare Hands", The Nation's Hospitals & Diagnostic Laboratories, Fall 1975.

Comparison of Tracheobronchial Suction Catheters in Humans, *Chest*, vol. 69, pp. 179-181, Feb. 1976.

Selective Tracheobronchial Aspiration, *Thorax*, 32, 346-348, 1977.

Efficon Trach Care Brochure and Price List, Apr. 15, 1978.

A New Controllable Suction Catheter for Blind Cannulation of the Main Stem Brochi, *Critical Care Medicine*, vol. 6, No. 5, Sep.-Oct. 1978.

Disposable Suction Catheter, *Nursing*, May 1979.

Evaluation of Selective Brochial Suctioning in the Adult, *Critical Care Medicine*, vol. 8, No. 12, 1980.

Design and Funtion of Tracheal Suction Catheters, 1982.

The New NL Tracheal Suction Catheter, *Anesthesiology*, 1982.

Selective Bronchial Suctioning in the Adult Using a Curved-Tipped Catheter with a Guide Mark, *Critical Care Medicine*, vol. 10, No. 11, Nov. 1982.

Device for Determining Location of an Endotracheal Catheter Tip, *Critical Care Medicine*, vol. 12, No. 2, Feb. 1984.

The Bear NVM-1 Neonatal Volume Monitor, 1986, [citing U.S. Pat. No. 4,363,238].

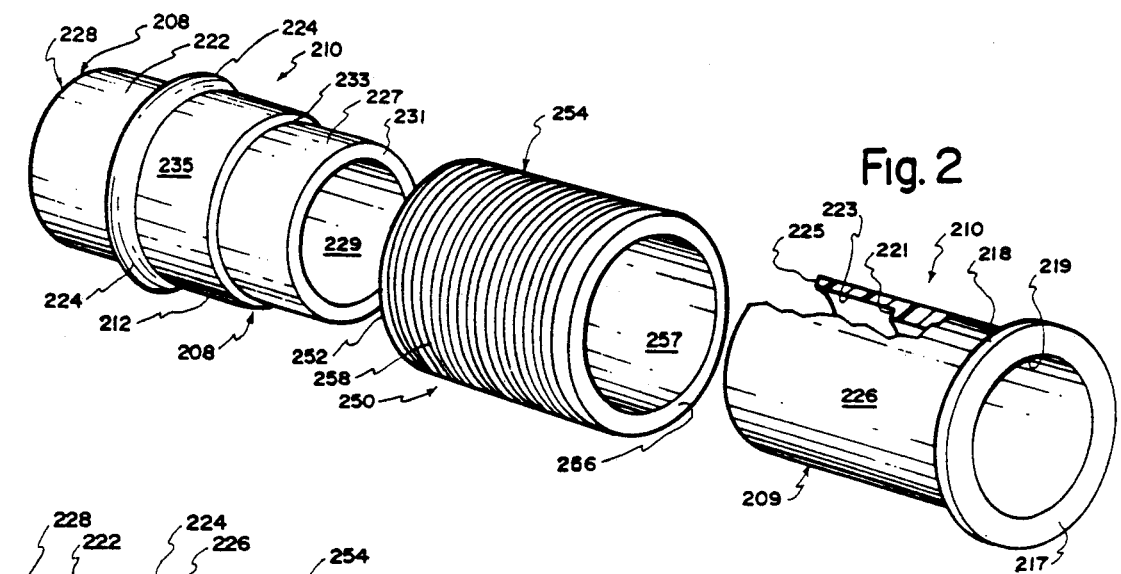
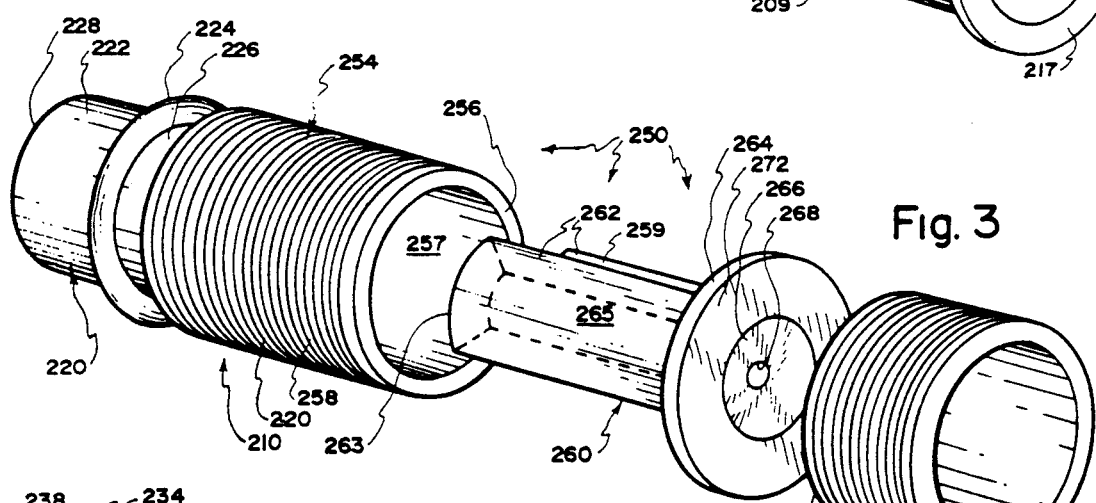
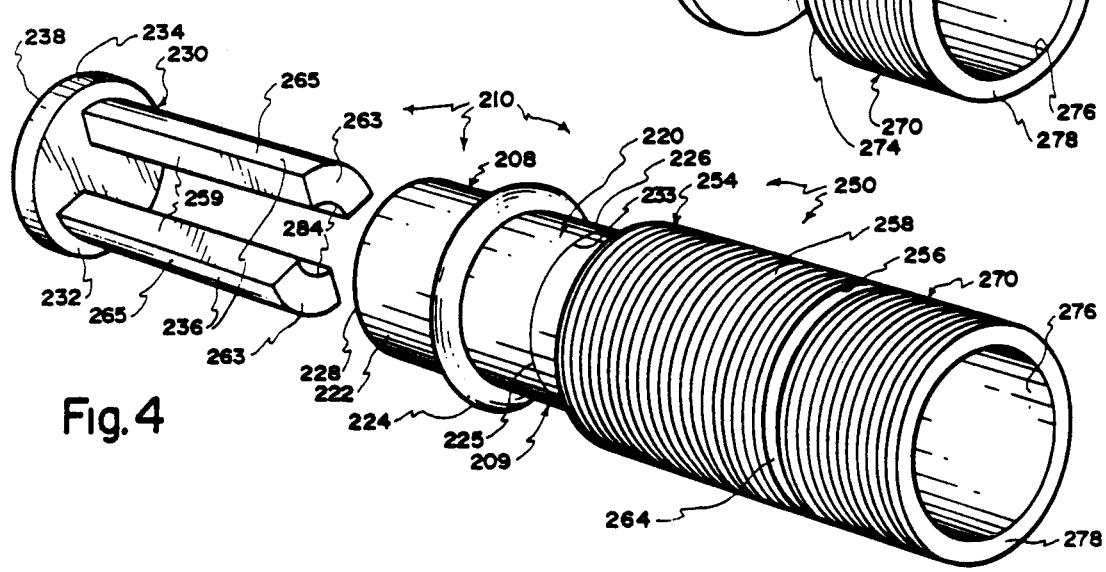

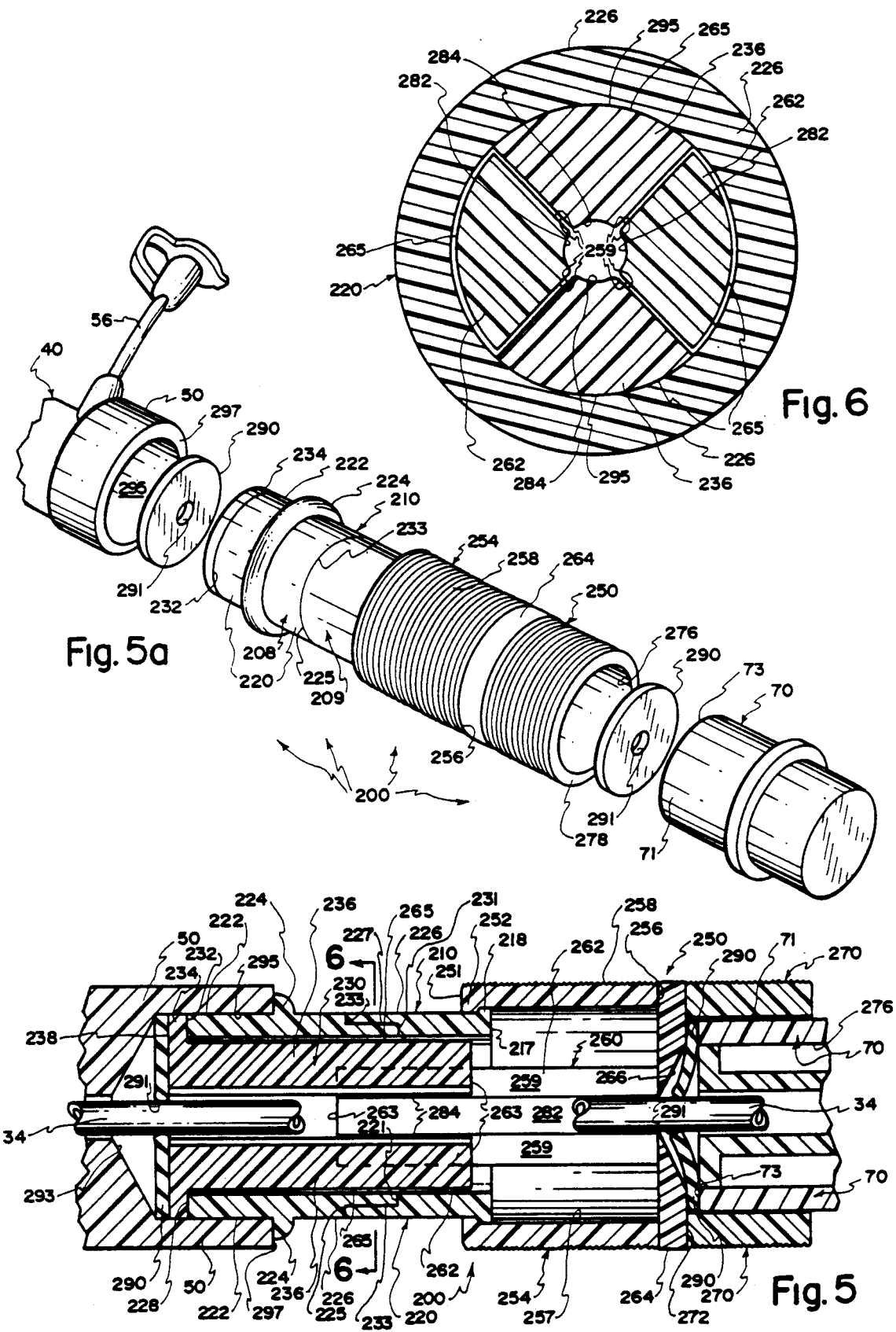

ASPIRATING CATHETER TUBE INSERTER

FIELD OF INVENTION

The present invention relates generally to involuntary ventilation of the respiratory system of a medical patient and involuntary aspiration of secretions from the lungs of the patient and, more particularly, to a novel aspirating catheter tube insertion mechanism, and related methods, which is particularly useful with neonatal aspirating catheter tube insertion, the insertion mechanism being used to provide accurate, facile, safe, and effective indwelling displacement of the aspirating catheter tube whereby accumulated secretions are selectively evacuated from the lungs.

BACKGROUND

Removing secretions from the lungs of a medical patient has presented problems for a long time. This is particularly true of secretion removal from an infant. As described in U.S. Pat. No. 4,838,255, respiratory distress frequently occurs in infants and small children experiencing respiratory problems. This is commonplace in premature infants. When an infant or small child is unable to breathe adequately on its own, intubation and involuntary ventilation is provided via an endotracheal tube. This requires periodic, involuntary removal, via a small suction or aspirating catheter tube, of secretions which accumulate in the lungs. Catheter insertion should be accurately accomplished without injury to or penetration of the lungs by the catheter tube. Percise control in placement of the suction catheter tube is of great concern because of the risk of trauma, injury and death as a result of placement.

Known patents concerning catheter insertion are U.S. Pat. No. 4,838,255 (mentioned above) and U.S. Pat. Nos. 3,444,860, 3,894,540, and 4,062,363. U.S. Pat. 4,838,255 is related to respiratory and aspirating systems for intubated patients, including infants. U.S. Pat. Nos. 3,444,860 and 3,894,540 are related to urinary catheters, and U.S. Pat. No. 4,062,363 relates generally to catheter insertion.

Apparatus and procedures currently available rely upon tactile senses and motor skills of medical technicians to accurately control aspirating catheter insertion so as to minimize trauma and risk to the patient. For example, U.S. Pat. No. 4,838,255 discloses a static insertion guide and flexible cover which allows a technician to grasp the aspirating catheter through the cover and carefully thread the catheter along the static insertion guide into a patient's lungs.

U.S. Pat. No. 3,444,860 discloses an aseptic catheter assembly with a holder introducer which is primarily meant for use in the urinary tract. A catheter assembly including a lubricated urinary catheter tube with a collection bag connected to one end and an elongated hollow, open-ended semi-rigid holder-introducer is described. An elongated tubular membrane surrounds the holder-introducer and is connected to the catheter tube on one end such that, as the tublar membrane is telescopically forced over the holder-introducer, the catheter tube is forced from the holder-introducer into an ingress site. Tactile sensing and pressure control upon an inserted catheter is not particularly sensitive.

A urinary catheter comprising a telescoping or accordianated sheath is disclosed in U.S. Pat. No. 3,894,540. The catheter tube is inserted by serially grasping the catheter tube through the sheath and manually pushing the unfolding or telescopically extending sheath and substantially rigid catheter tube toward the point of catheter tube ingress. The catheter tube proceeds outward from the sheath and threads through the ingress site. Each time the catheter tube and sheath are released, the sheath relaxibly retruns to a less extended state such that the insertion step can be repeated. This provides for continuously inserting the catheter tube while maintaining catheter sterility, but requires gripping the catheter tube through a sheath whereby the "feel" of the catheter tube is acquired through a cover.

U.S. Pat. No. 4,062,363 discloses a telescoping or accordianated sheath having urinary and tracheal purposes. In the tracheal application, significant care must be taken to assure against too much pressure being applied when delivering a catheter tube into the lungs. This, as is true of each of the other previously described art, relies upon "feel" through a secondary cover to provide the feedback impedance to inward delivery of a catheter tube. The forces generating such "feel" are the sum of the catheter delivery retarding forces comprising the catheter feed system, the impeding factors of the patient's lung tissue and channels, and the compliance of the covering sheath which, especially when the attending technician is wearing surgical gloves, may not provide adequate retarding force feedback to signal the actual conditions which impede delivery of the catheter tube into a lung.

BRIEF SUMMARY AND OBJECTS OF THE INVENTION

In brief summary, this novel invention is intended to overcome or substantially alleviate limitations of the prior art and comprises novel inserter structure, and related methods, for inserting and aspirating catheter tube into a patient's trachea and lungs. The invention is particularly useful for, although not limited to, insertion into the lungs of an infant.

The present invention features novel inserters, and related methods, for accurate and non-injurious placement of an aspirating catheter tube in a desired lung position in a patient. The invention provides for facile, injury-free, incremental and accurate delivery of an aspirating suction catheter tube into a desired lung location within the respiratory system of the patient through use of the catheter inserter.

The inserter relies upon the simultaneous application by the inserter of resilient drag upon the catheter tube as it is compressively and resiliently grasped and incrementally advanced by manual linear advancement of the inserter. A manual squeezing force is not required. If advancement of the catheter tube toward a desired lung site meets with undue resistance, the inserter merely slides forward along the catheter tube. During the return stroke of the inserter, the catheter tube is resiliently and compressively held stationary while the inserter is retracted such that the resilient grasping site is frictionally displaced with the inserter along the outside surface of the catheter tube. Guide structure is provided to accommodate linear, non-binding reciprocation of the inserter. Removal or egress of the catheter tube from a lung site is achieved by merely applying a pulling force directly to the catheter tube sufficient to overcome the drag exerted upon the catheter tube at the resilient grasping and drag sites, which may comprise elastomeric washers that are selectively flexed by reason of engagement with the catheter tube.

With the foregoing in mind, it is a primary object of the present invention to provide an inserter, and related methods, which is compatible with a ventilating and/or aspirating mechanism and accommodates facile, accurate and injury-free delivery of an aspirating catheter tube to a desired lung site.

Another valuable object is the provision of an inserter for an aspirating catheter tube, and related methods, which overvcome or substantially alleviate problems heretofore existing in the relevant art.

It is an important object of the present invention to provide a movable housing which is facilely gripped and which, in combination with a catheter inserter, conditionally moves a catheter tube toward a distal ingress site when the movable housing is displaced distally by the operator and which does not move the catheter tube when the movable housing is displaced proximally.

Another paramount object of the present invention is the provision of a novel aspirating catheter tube inserter which relies upon the simultaneous application of resilient drag upon the catheter tube as it is compressively and resiliently advanced by manually linear advancement of the inserter.

It is another dominant object to provide a novel inserter for advancement of an aspirating catheter tube toward a desired lung site which, if advancement of the catheter tube toward a desired lung site meets with undue resistance, the inserter merely slides forward along the catheter tube.

A further important object is the provision of a unique aspirating catheter tube inserter wherein a manual squeezing force is not required.

An additional significant object is the provision of a novel aspirating catheter tube inserter which, during the return stroke of the inserter, the catheter tube is resiliently and compressively held stationary while the inserter is retracted such that a resilient grasping site is frictionally displaced with the inserter along the outside surface of the catheter tube.

It is also significant to provide an inserter comprising novel guide stgructure which accommodates liner nonbinding reciprocation of the inserter.

Another principal object of the present invention is the provision of a novel inserter for advancing an aspirating catheter tube wherein removal or egress of the catheter tube from a lung site is achieved by merely applying a pulling force to the catheter tube sufficient to overcome drag exerted upon the catheter tube at resilient grasping and drag sites.

A further valuable object is the provision of a novel inserter for an aspirating catheter tube, which comprises elastomeric washers that are selectively flexed by reason of engagement with the catheter tube.

These and other objects and features of the present invention will be apparent from the detailed description taken with reference to accompanying drawings.

BRIEF DESCRIPTION OF THE DRAWINGS

FIG. 2 is an exploded perspective of cylindrical segments of a non-moving or stationary part of the inserter of FIG. 1;

FIG. 3 is a persepctive of part of the inserter of FIG. 1, with the components of FIG. 2 shown in an assembled condition and a further movable housing member guide segment, and a serrated end connector segment shown in an exploded condition;

FIG. 4 is a perspective of the inserter of FIG. 1 showing the components illustrated in FIG. 3 in an assembled condition and further depicting a stationary guide member in an exploded condition;

FIG. 5 is a cross sectional view taken along lines 5—5 of FIG. 1;

FIG. 5a is an exploded, perspective view of the fully assembled inserter of FIG. 1 with associated portions of the ventilating and aspirating assembly of FIG. 1 illustrated in perspective.;

FIG. 6 is a cross section of the invention taken along lines 6—6 of FIG. 5;

DETAILED DESCRIPTION OF THE ILLUSTRATED EMBODIMENT

In this description, the term "proximal" is used to indicate a segment of a device or part thereof normally closer to an operator (farther from a patient) when it is in use. The term "distal" refers to the segment of the device or part thereof farther from the operator and, therefore, closer to the patient.

Figure 1:
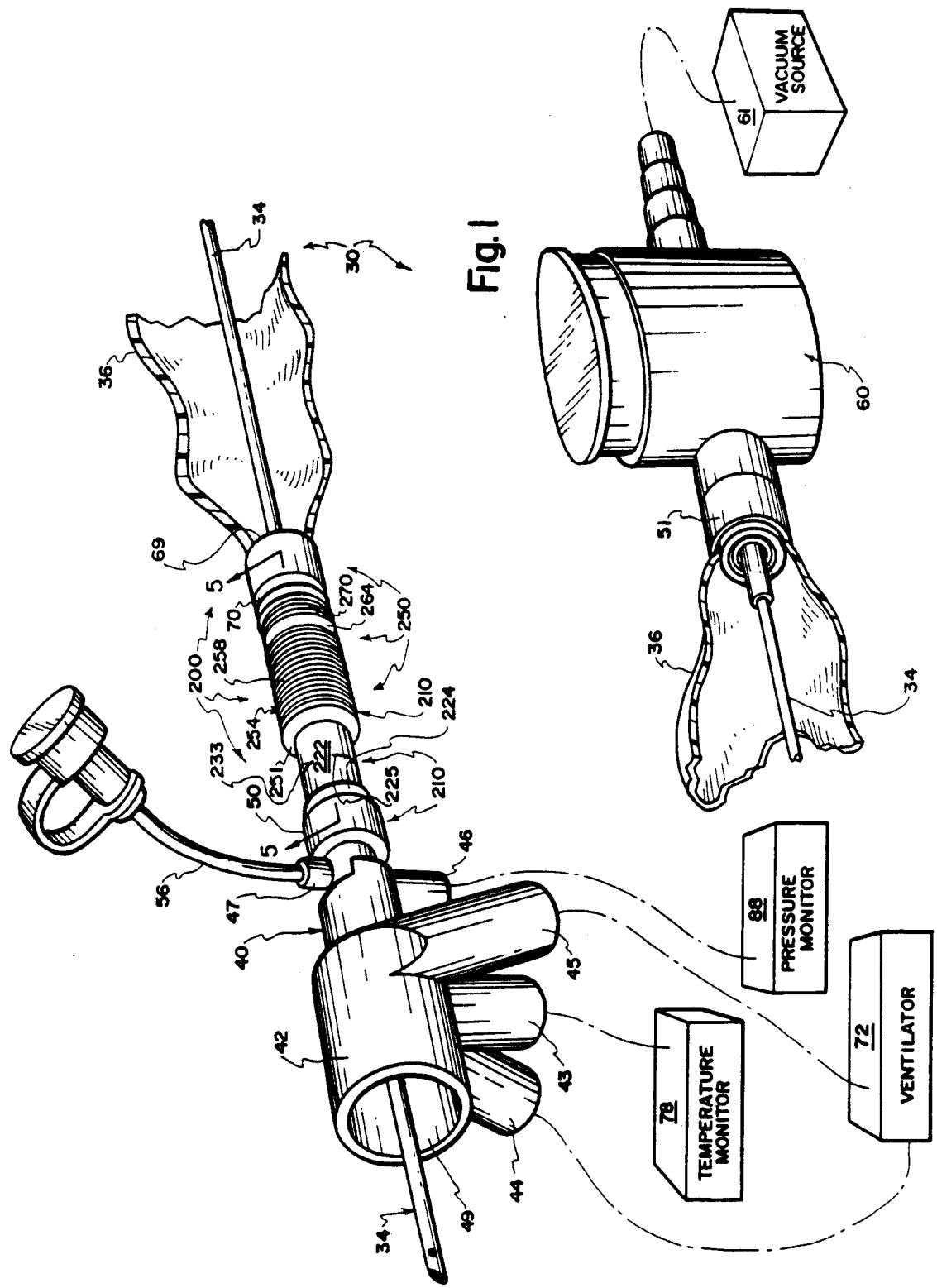
FIG. 1 is a perspective of one presently preferred inserter according to the invention interposed between otherwise connecting segments of a ventilating and aspirating assembly comprising an aspirating catheter tube.

Reference is now made to the embodiment illustrated in FIGS. 1-8 wherein like numerals are used to designate like parts throughout. A presently preferred inserter embodiment is illustrated in FIG. 1 and generally designated 200. Inserter 200 is interposed between two other segments of an aspirating and ventilating mechanism 40, although the invention is not limited by the specific ventilating and aspirating configuration herein disclosed. The ventilating and aspirating mechanism 40 is illustrated as comprising a distal fitting 42 which comprises access port 43 for a temperature monitor 78, ports 44 and 45 for a ventilator 72, port 46 for a pressure monitor 88, and port 47 for attachment to a liquid introducer 56 (for lavage and like liquids). The distal fitting 42 telescopically couples at its proximal end to a collar connecter 50, which in turn telescopically couples to the inserter 200. Fitting 42 comprises a relatively large distal barrel 49 which is adapted to be pressfit upon the exposed proximal end of an indwelling endotracheal tube. Exclusive of inserter 200, fitting 42 and its appurtenances are illustrated as being substantially identical to the corresponding fitting disclosed in U.S. Pat. No. 4,838,255, the contents of which are incorporated herein by reference.

Connected to the proximal end of the catheter tube inserter 200 is a collapsible catheter sheath 36. A forcefit collar 69 releasably connects the distal end of the sheath 36 to proximal end fitting 70 of the inserter 200.

An aspirating catherer tube 34 linearly passes through the hollow interiors of fitting 42, collar 50, inserter 200 and fitting 70. The sheath 36 is secured on the other end at force-fit collar 51 to an aspiration control valve 60. The proximal end of valve 60 connects to a vacuum source 61. Further structural operational details of the ventilating and aspirating apparatus 40, including vacuum valve 60 are provided in U.S. Pats. No. 4,569,344 and 4,838,255, to which reference may be made.

Inserter 200, as illustrated, comprises a slidable housing 250 and a stationary housing 210. Stationary housing 210 telescopically fits into and is secured at collar 50, while slidable housing 250 telescopically internally receives fitting 70 at the proximal end thereof when assembled to be part of the ventilating and aspirating system 40 whereby aspirating catheter tube 34 is facilely, accurately, and safely delivered to a desired lung site of the patient. Such delivery is of particular significance to neonatals.

Unless otherwise herein stated, the components of inserter 200 are preferably formed of suitable synthetic resinous material, preferably using conventional injection molding techniques. The construction and assembly of the inserter 200, including assembling of the movable housing 250 and the non-movable housing 210 is best understood by reference to FIGS. 2-4, wherein it can be seen that movable housing 250 comprises a distal externally serrated, hollow cylinder 254, a pronged proximal guide 260, a shorter, proximal, externally serrated cylinder 270 and fitting 70.

Non-movable housing 210 comprises two cylinder segments 208 and 209, which are joined at a cylindrical lap joint to form assembled cylinder 220, and a distal pronged or finger guide 230. As seen in FIg. 2, cylinder segment 209 comprises a proximal radially outwardly extending flange segment 218 defining a hollow interior at 219 and comprising radially-directed blunt end edge surface 217 and proximal outer cylindrical surface 226. The hollow interior at 219 of the cylindrical segment 209 is illustrated as being of uniform diameter from edge 217 in a distal direction until interior shoulder 221 is reached. At shoulder 221, the diameter at surface 223 of cylindrical segment 209 is enlarged to a greater inside diameter which remains constant from the shoulder 221 to blunt distal edge surface 225.

Cylindrical segment 208 comprises a proximal cylindrical wall segment 227 defining a hollow interior 229, the diameter of which is the same as at 219. This diameter is uniform throughout the axial length of cylindrical segment 208. Well segment 227 is of uniform thickness and extends distally from proximal blunt edge 231 to stepped shoulder 233. The axial length and diameter of wall segment 227 are respectively essentially the same as the axial length and diameter of wall surface 223. At shoulder 233, the wall thickness increase, i.e., along wall segment 235. The outside diameter of wall segment 235 is the same as the diameter of wall surface 226. Cylindrical segment 208 also comprises a medial outwardly-directed flange segment 224, distal outer cylindrical surface 222 and a distal end edge surface 228.

Distal serrated cylinder 254 comprises an outer distal serrated cylindrical surface 258, a smooth cylindrical interior surface 257 of predetermined diameter, a planar or blunt proximal end edge surface 256, and a distal end edge surface 251 forming part of an inwardly directed, radially directed flange 252. The serrated surface area, at 258, and internal diameter, at 257, of distal serrated cylinder 254 are of such a size that movable housing 250 may be facilely grasped between forefinger and thumb and moved reciprocally back and forth longitudinally, yet large enough that movable housing 250 slides reciprocally closely to but smoothly, without binding, over the desired portion of the non-movable housing 210, which contains guide fingers and a channel through which the aspirating catheter tube 34 is selectively displaced.

The proximal flange segment 218 of cylinder segment 209 is inserted telescopically into the proximal end of serrated cylinder 254 so as to be located proximal of internally-directed flange 252 of serrated cylinder 254. See FIG. 5. Once so inserted, with the serrated cylinder retracted, cylinder segments 208 and 209 are telescopically united and bonded, using a suitable adhesive or other conventional bonding or plastic welding techniques, primarily along the contiguous surfaces at 223 and 227 to form cylinder 220.

FIG. 3 shows further parts required to complete the movable housing 250. These parts comprise proximal pronged or finger guide 260 and proximal serrated cylinder 270. Distally-extending guide fingers 262 of proximal guide 260 are inserted into the hollow interior at 257 of the distal serrated cylinder 254 and rigidly connected to cylinder 220. Though the guide fingers 262 can be formed in many other ways, in this embodiment, each distally-extending guide finger 262 is an arcuate segment of a hollow cylinder which subtends an angle of 90° between surfaces 259. Each finger 262 is substantially the same as either finger 236 and, accordingly, is of a longitudinal distance slightly less than the length of the cylinder 210, ends in a blunt end edge 263, defines an outside diameter at surface 265 which is just slightly less than the inside diameter of cylinder 210 and comprises an inside surface 282 (FIG. 6) of a diameter to accommodate catheter tube advancement and retraction adjacent thereto. Thus, a pathway between the two catheter guide surfaces 282 is formed.

Proximal guide 260 comprises a proximal flange or end plate 264, which is substantially the same diameter as the outer diameter of serrated surface 258 of distal cylinder 254 such that, when proximal guide 260 is completely and properly assembled within the movable and non-movable housing cylinders 210 and 250, flange plate 264 is contiguous with and adhesively bonded to serrated distal cylinder 254 at surface 256 to provide an outer cylindrical surface of essentially uniform diameter with serrated surface 258. Thus, guide 260 moves with cylinder 254, which manually reciprocates, as explained herein in greater detail.

Serrated proximal cylinder 270 also comprises an outside diameter, which is substantially the same as serrated distal cylinder 254 and proximal guide 260. Cylinder 270 further comprises distal planar blunt edge surface 274, which correspondingly matches planar proximal face 272 of flange plate 264. Serrated proximal cylinder 270 is contiguously bonded to proximal guide 260 to complete movable housing 250 having a uniform outer cylindrical surface as shown in FIG. 4. Thus, both guide 260 and cylinder 270 move with cylinder 254 as cylinder 254 is reciprocated manually.

Assembled cylinder 220 further comprises a medial stop flange 224, which functions as an abutment limiting distal travel of movable housing 250, the contact between the flange 251 at surface 252 against flange 224 functioning to cause the movable housing 250 to distally stop. Similarly, engagement of flange 251 with flange 252 during retraction causes the movable housing to proximally stop. See FIG. 5. In combination, these two stops define the length of travel of movable housing 250 relative to stationary housing 210 and, as described in greater detail later, further determine maximum catheter tube travel with each inserter stoke, i.e., each reciprocal cycle of the movable housing.

Extending distally beyond the medial, outwardly-directed flange 224, assembled cylinder 220 comprises distal exposed exterior surface 222, which ends at distal edge 228. In complementary fashion to distally-extending guide fingers 262 described above, distal guide 230 comprises two proximally-extending guide fingers 236, which are essentially identical to fingers 262 and, unless otherwise indicated, have been so identified in the drawings. A cylindrical pathway between internal cylindrical catheter guide surfaces 284 is formed for catheter tube reciprocation. The length or lengths of each of the distally-extending guide fingers 262 and proximally-extending guide fingers 236 are short enough that none limits distal travel of movable housing 250 while each is sufficiently long that they continue to function to insure linear, nonbinding reciprocation of the movable housing 250, even when fully proximally retracted. As can best be seen in FIG. 6, the fingers 236 are radially placed 90° out of phase with respect to fingers 262 to accommodate said non-binding linear reciprocation.

FIG. 5 is a longitudinal cross section of the assembled catheter tube inserter 200 taken along lines 5—5 of FIG. 1. Flange 252 of cylinder 254 is illustrated as having been positioned distally beyond flange 218. Stationary guide 230 has been fully telescopically extended into the hollow center of cylinder 210 so that the peripheral edge of flange 234 is flush with the outside diameter of cylinder 210 at surface 222 and the flange 234 is contiguously bonded at interface 232 to the blunt distal edge 228. Surfaces 265 of finger 236 are contiguously bonded to the inside surface of the cylinder 210 with interfaces 295.

FIG. 5 also shows distal washer 290 as having been placed resiliently compressively, though relatively reciprocably, over the outer surface of catheter tube 34 at aperture 291 and placed within counterbore 293 of collar 50 (to allow washer flexing, as explained later in greater detail). The distal surface 222 of the cylinder 210 is shown in FIG. 5 as having been substantially contiguously inserted into the proximal bore 295 of the collar 50 and bonded in that position, leaving annular rib 224 exposed but contiguous with proximal end edge 297 of the collar 50. Thus, guide 230 and cylinder 210 are immovably connected to collar 50, leaving the distal catheter tube restraining washer 290 internally disposed for flexing adjacent surface 293 responsive to manual displacement of the movable housing 250.

Also, in FIG. 5, guide 260, comprising one part of the movable housing 250, is shown in its fully retracted position.

In FIG. 6, which is a cross sectional view taken along lines 6—6 of FIG. 5, proximally and distally extending guide fingers 236 and 262, respectively, are shown surrounded by the cylinder 220. As mentioned earlier, each guide finger 236, 262 subtends an angle of 90° from a point just proximal from the center of the inscribed hollow cylinder and, therefore, the oppositely directed guide arms slide relatively against each other along surfaces 259 to maintain alignment and to prevent binding as movable housing 250 is linearly reciprocated along non-movable housing 210. The guide fingers comprise catheter tube-receiving guide surfaces 282 and 284, which collectively provide a channel or bore of sufficient diameter that the catheter travels back and forth therethrough without binding or kinking.

The remaining structure and assembly of the inserter 200 will not be described. In reference to FIGS. 5 and 5a, proximal catheter tube-restraining washer 290 is placed snugly, resiliently and compressively over the catheter tube 34 and inserted into the hollow interior 276 of serrated ring 270 until the washer is contiguous with the surface 272 of plate 264.

The proximal male connector 70 is telescopically inserted at leading end 71 thereof snugly into the hollow interior 276 of the ring 270 and there contiguously bonded in place so that the distal edge 73 thereof is contiguous with the proximal surface of the proximal washer 290. See FIG. 5. Thus, the proximal washer 290 is trapped as shown in FIG. 5, but space adjacent counterbore surface 266 is provided in which the washer flexes, as explained herein in greater detail.

Each washer 290, when installed, compressively bites against catheter tube 34. The catheter tube is moved forward by the inserter 200, because the proximal washer 290 seizes or grips against the surface the catheter tube so that the movable housing 250 and the catheter tube 34 are displaced together.

At the beginning of the advancement stroke, distal washer 290 is disposed vertically, as shown in FIG. 5. However, as manual displacement of movable housing of the inserter 200 moves catheter tube 34 ahead, via the gripping action of proximal washer 290 at aperture 291, the catheter tube 34 slides tightly through the aperture 291 of the distal washer 290. This flexes the distal washer to the position of FIG. 7 and applies an insertion control drag to the displacement of the catheter tube.

Thus, the counterbore defined by surface 293 provides freedom of movement for the distal washer 290 to be so flexed or distorted as the catheter tube 34 is advanced. Similarly, the proximal washer 290 is flexed or distorted into the counterbore adjacent surface 266 during retraction of the movable housing, during which time the distal washer 290 holds the catheter tube stationary and the proximal washer 290 slides along the catheter tube 34.

Manual pulling on the catheter tube 34 will override the resistance of both washers 290 for rapid withdrawal of the catheter tube. The force required to distort each washer 290 into the associated counterbore is less than the seizing force of each seal washer 290 against catheter tube 34.

Figure 7:
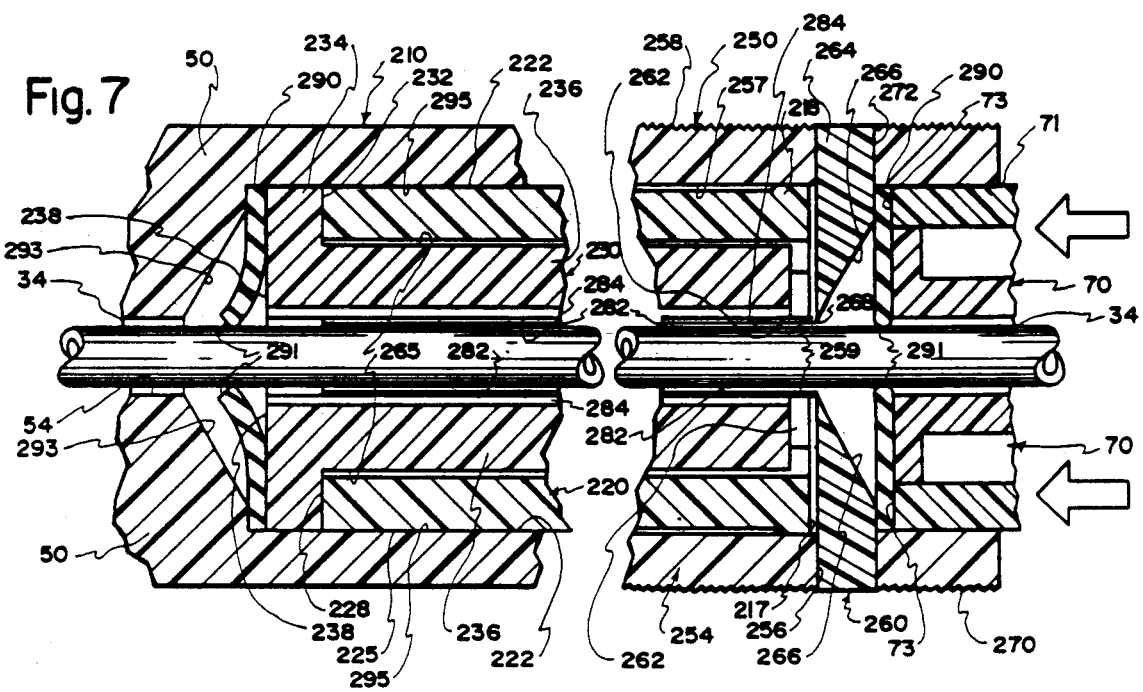
FIG. 7 is a cross section similar to FIG. 6 but showing the disposition of the catheter tube restraining washers when the movable housing of the inserter is moved toward the patient.
Figure 8:
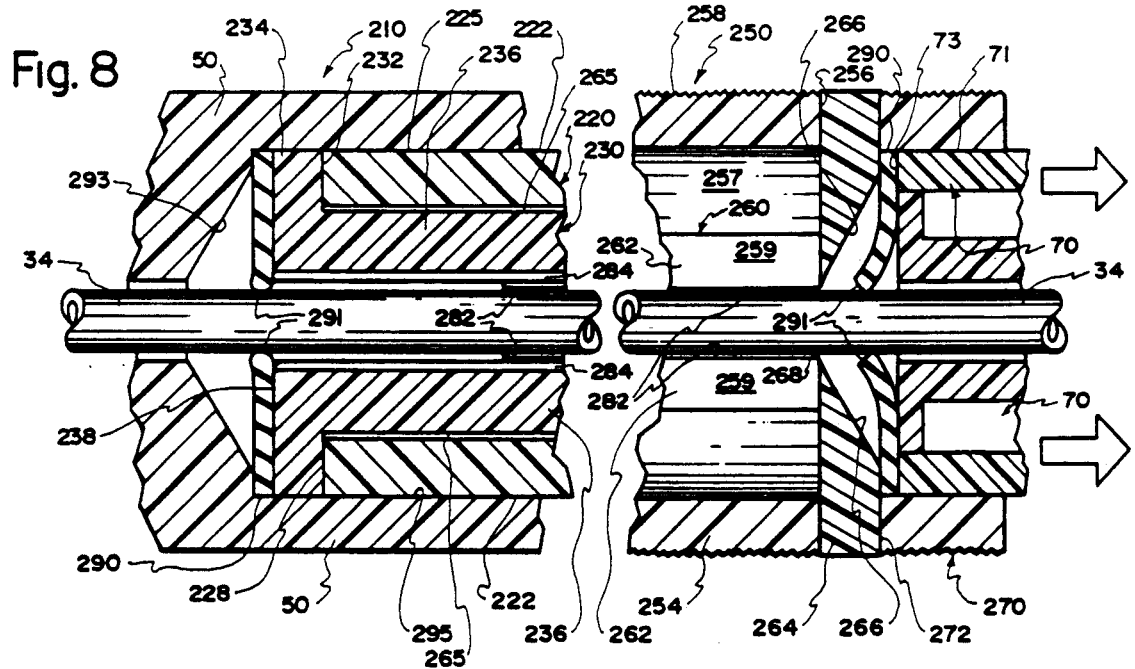
FIG. 8 is a cross section similar to FIGS. 6 and 7 but showing the disposition of the catheter tube restraining washers when the movable housing of the inserter is moved away from the patient.

Delivery of catheter tube 34 to a desired lung site is understood better by reference to FIGS. 7-8. As shown in FIG. 7, when movable housing 250 is being pushed distally, the manual force of displacement is transferred from the housing 250 to the proximal washer 290 and thence to the catheter tube 34 thereby moving the catheter tube 34 distally. Distal washer 290, because it is compressively engaging the catheter tube 34, follows the movement of catheter tube 34 until flexed so that the catheter tube begins to slide through the aperture 291 of the distal washer 290, distal washer 290 continuing to apply a drag to catheter tube which enhances manual control of and precision in achieving lung insertion. Catheter tube 34 is thus resistantly advanced into the patient's lung through the distance movable housing 250 is manually distally advanced unless the catheter tube has been inserted the maximum distance allowed by its physical length of the catheter tube or there is a retarding force which prevents further displacement. Thus, the delivery force required for catheter tube insertion is uniform and greater than the drag caused by the distal washer 290, thereby improving control.

Abrupt delivery against retarding lung tissues because a lack of resistance is avoided. Thus, the possibility of patient injury during catheter delivery is at least substantially reduced.

When movable housing 250 is moved proximally or retracted after having been fully advanced, the catheter tube 34 is held essentially stationary by the compressive force exerted thereon by the distal washer 290. The proximal washer 290 flexes and wipes against the catheter tube 34 at aperture surface 291, which involves approximately the same resistance to displacement as with the advancement stroke. Restated, reciprocal movement of movable housing 250 only incrementally moves the catheter tube 34 distally.

Retraction of the catheter tube from the lungs is accomplished by grasping the catheter tube 34 through covering sheath 36 and pulling it proximally, whereby the catheter tube is fully returned into the sheath 36 against the drag caused by washers 290.

Movable housing 250 and stationary housing 210 are preferably injection molded or otherwise molded or machined preferably from substantially rigid suitable synthetic resinous materials which comprise polyethylene, polymethylmethacrylate or polystyrene. Washers are made from a suitable compressible and compliant synthetic resinous materials, such as silicon rubber. The material selected for washers preferably has an adequate coefficient of friction such that washers restrainingly and resiliently compressively grip the catheter tube 34 and prevent movement of the catheter tube, when movable housing 250 is linearly moved proximally, and seize and force the catheter forward, when movable housing 250 is moved distally. Washers 290 have sufficient compliance to release seizure of the catheter tube when there is no retarding wall which forces the washer to remain in orthogonal relationship with the catheter tube as the catheter tube moves. The binding frictional force, which is a function of the coefficient of friction and the degree of compression of each washer 290 when the washer is positioned in a plane orthogonal to the catheter, is limited to less than a catheter tube insertion force which would cause tissue injury to lung tissue or the like.

The invention may be embodied in other specific forms without departing from the spirit or essential characteristics thereof. The present embodiment is therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed and desired to be secured by Letters Patent is:

1. An inserter for placement of a distal end of an aspirating catheter tube at a desired lung site, the inserter comprising:

first tube inserting housing means through which the catheter tube reciprocably extends;

first elastomeric means associated with the first tube inserting housing means and comprising aperture means of a diametral size less than the diameter of the catheter tube resiliently compressively engaging the catheter tube at a first site;

second tube inserting housing means reciprocably associated with the first tube inserting housing means and through which the catheter tube reciprocably extends;

second elastomeric means associated with the second tube inserting housing means and comprising aperture means of a diametral size less than the diameter of the catheter tube resiliently compressively engaging the catheter tube at a second site;

whereby manual distally directed displacement of the second tube inserting housing means in respect to the first tube inserting housing means causes the aperture means of the second elastomeric means to grippingly distally advance the catheter tube and the aperture means of the first elastomeric means to exert a displacement controlling drag upon the distally advancing catheter tube and manual proximally directed displacement of the second tube inserting housing means in respect to the first housing tube inserting means accommodates holding by the aperture means of the first elastomeric means to hold the catheter tube against material displacement as the aperture means of the second means is displaced proximally along the catheter tube site.

2. An inserter for placement of a distal end of an aspirating catheter tube at a desired lung site, the inserter comprising:

first housing means through which the catheter tube reciprocably extends;

first means associated with the first housing means and comprising means resiliently compressively engaging the catheter tube at a first site;

second housing means reciprocably associated with the first housing means and through which the catheter tube reciprocably extends;

second means associated with the second housing means and comprising means resiliently compressively engaging the catheter tube at a second site;

each resilient compressive means comprising elastomeric means applying radial circumferential pressure upon the exterior of the catheter tube;

whereby manual distally directed displacement of the second housing means in respect to the first housing means causes the resiliently compressive means of the second means to grippingly distally advance the catheter tube and the resiliently compressive means of the first means to exert a displacement controlling drag upon the distally advancing catheter tube and manual proximally directed displacement of the second housing means in respect to the first housing means causes the resiliently compressive means of the first means to hold the catheter tube against material displacement and the resiliently compressive means of the second means to be displaced proximally along the catheter tube.

3. An inserter according to claim 2 wherein each elastomeric means comprises a washer comprising a central aperture through which the catheter tube passes, the aperture having an unstressed diameter less than the outside diameter of the catheter tube.

4. An inserter according to claim 3 wherein flex chamber means are disposed in each housing means adjacent each washer to allow selective central flexing of the associated washer in a desired direction.

5. An inserter according to claim 1 wherein the first tube inserting housing means are connected to a fitting adapted for connection to a proximal end of a patient respiratory tube.

6. An inserter according to claim 1 wherein the second tube inserting housing means are connected to the distal end of a collapsible sheath disposed at least in part over the catheter tube.

7. An inserter according to claim 1 wherein the first tube inserting housing means comprise distal stop means and proximal stop means which collectively define the reciprocable travel of the second tube inserting housing means.

8. An inserter according to claim 1 wherein the two tube inserting housing means comprise guide means which limit the displacement of the second tube inserting housing means to essentially linear displacement.

9. An inserter for positioning a distal end of an aspirating catheter tube at a desired lung site of a medical patient, the inserter comprising:
   first relatively stationary means comprising first site means which yieldably compressively grip the exterior of the catheter tube;
   second relatively reciprocable means comprising second site means which yieldably compressively grip the exterior of the catheter tube;
   whereby manual distal displacement of the second relatively reciprocable means in respect to the first relatively stationary means causes the second site means to distally advance the catheter tube and the first site means to exert a displacement controlling drag upon the distally advancing catheter tube and manual proximal displacement of the second means in respect to the first means causes the first site means to grip and statically hold the catheter tube against displacement while the second site means are displaced along the static catheter tube in a proximal direction.

10. A manual inserter which does not respond to manual compression for positioning a distal end of an aspirating catheter tube at a desired lung site of a medical patient, the inserter comprising:
    manual grasping means reciprocably associated with the catheter tube;
    elastomeric washer means carried by the manual grasping means which circumferentially yieldingly and compressively contiguously engage and grip the catheter tube;
    whereby manual reciprocal displacement of the manual grasping means correspondingly displaces the elastomeric washer means which causes only distal displacement of the catheter by reason of said yielding grip.

11. A method for placement of a distal end of an aspirating catheter tube at a desired lung site using an inserter, comprising the steps of:
    causing a first elastomeric part carried and protected from manual compression by an exposed non-compressible displacement housing of the inserter to externally and contiguously grip the catheter tube at one site so as to outwardly radially compress the first elastomeric part by selectively movable engagement with the catheter tube at the one site;
    causing a second elastomeric part carried by a stationary portion of the inserter to externally and contiguously grip the catheter tube at a second site so as to outwardly radially compress the second elastomeric part by engagement with the catheter tube at the second site;
    distally displacing the exposed housing so that the grip at the first site overcomes the grip at the second site to frictionally distally displace the catheter tube, the second elastomeric part exerting a displacement controlling drag upon the catheter tube as it is distally advanced.

12. A method for placement of a distal end of an aspirating catheter tube at a desired lung site using an inserter, comprising the steps of:
    causing a first elastomeric part carried and protected from manual compression by an exposed non-compressible displacement housing to externally and contiguously grip the catheter tube at one site so as to outwardly radially compress the first elastomeric part against the catheter tube at the one site;
    causing a second elastomeric part carried by a stationary portion of the inserter to externally and contiguously grip the catheter tube at a second site so as to outwardly radially compress the second elastomeric part against the catheter tube at the second site;
    distally displacing the exposed housing so that the grip at the first site overcomes the grip at the second site to frictionally distally displace the catheter tube, the second elastomeric part exerting a displacement controlling drag upon the catheter tube as it is distally advanced;
    discontinuing the distal displacement;
    proximally displacing the exposed housing so that the grip at the second site holds the catheter tube in an essentially stationary disposition and the grip at the first site changes from static to dynamic thereby accommodating the proximal displacement of the first elastomeric part along the catheter tube.

13. An aspirating catheter tube insertion system used to facilely, safely, and efficiently deliver the aspirating catheter tube to the lungs of a patient through an ingress fitting comprising:
    an aspirating catheter tube to be delivered to a patient's lungs for the purpose of medical therapy comprising suctioning;
    an endotracheal fitting;
    a catheter inserter comprising stationary housing means connected to the fitting, the stationary housing means comprising at least first seizing and releasing means which are deformingly compressed against the catheter tube, and movable housing means reciprocably associated with the stationary housing means, the movable housing means comprising at least second seizing and releasing means which are deformingly compressed against the catheter tube;
    whereby manual distally directed displacement of the movable housing means in respect to the stationary housing means causes the second seizing and releasing means to distally advance the catheter tube and the first seizing and releasing means to exert a displacement controlling drag upon the distally advancing catheter tube by reason of said deforming compression and whereby manual proximally directed displacement of the movable housing means in respect to the stationary housing means causes the first seizing and releasing means to hold the catheter tube essentially stationary against material displacement while the second seizing and releasing means are slidingly and contiguously displaced proximally along the catheter tube.

* * * * *